United States Patent [19]

Jessel, Jr. et al.

[11] Plant 4,220

[45] Mar. 7, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 780,984

[22] Filed: Mar. 24, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

An induced mutation of Frost characterized by its yellow ray florets.

1 Drawing Figure

The present invention comprises a new and distinct cultivar of *Chrysanthemum morifolium* Ramat., hereinafter referred to by the cultivar name Yellow Frost (#72072B13).

Yellow Frost is a product of planned sport induction program which had the objective of expanding the color range of the parental cultivar, Frost (#72072013: disclosed in our U.S. Plant patent application filed Aug. 23, 1976, Ser. No. 716,438).

Yellow Frost was discovered and selected by William E. Duffett and Walter H. Jessel, Jr. on May 20, 1975 as one plant within a flowering block of Frost in a controlled environment in Barberton, Ohio. Plants within the flowering block were derived from stock plants which had been irradiated as rooted cuttings with an x-ray source of 1800 r units.

The first act of asexual reproduction of Yellow Frost was accomplished when vegetative cuttings were taken from the initial selection in October, 1975 in a controlled environment in Barberton, Ohio by a technician working under formulations established and supervised by Walter H. Jessel, Jr. and William E. Duffett. Horticultural examination of selected units initiated Mar. 29, 1976 has demonstrated that the combination of characteristics as herein disclosed for Yellow Frost are firmly fixed and are retained through successive generations of asexual reproduction.

Yellow Frost has not been observed under all possible environmental conditions. The phenotype may vary significantly with variations in environment such as temperature, light intensity, and day length. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Yellow Frost which in combination distinguish this chrysanthemum as a new and distinct cultivar:

1. Spooned daisy capitulum type.
2. Flat capitulum form.
3. Medium yellow ray floret color.
4. Yellow-green (immature) to yellow (mature) disc floret color.

5. Diameter across face of capitulum from 80 to 95 mm. at maturity.
6. Uniform 9 week flowering response to photoperiodic short-day control.
7. Medium plant height (requires 1–2 long day weeks prior to short days to obtain a flowered plant height of 72 to 82 cm. when grown as a single stem plant for May through October flowerings.)
8. Semi-spreading branching pattern.
9. Minimal pollen development.

The accompanying color photographic drawing shows typical inflorescence and foliage characteristics of Yellow Frost. Color representations are as nearly true as possible with illustrations of this type.

Of the many commercial cultivars known to the present inventors, the most similar existing cultivar in comparison to Yellow Frost is the parental cultivar, Frost. Reference is made to attached Chart B which compares certain characteristics of Frost with the same characteristics of Yellow Frost. As noted in Chart B, the primary distinguishing characteristic of Yellow Frost in comparison to Frost is that of ray floret color. All other characteristics of Yellow Frost are similar to those same characteristics of Frost.

In the following description, color references are made to The Munsell Limit Color Cascade, 1972 edition. The color values were determined between 3:30 and 4:00 P.M. on Dec. 30, 1976 under 150 foot-candle light intensity at Barberton, Ohio.

Botanical classification: *Chrysanthemum morifolium*, Ramat., cv Yellow Frost.

INFLORESCENCE

Capitulum:

*Form.*—Flat.

*Type.*—Spooned daisy.

*Diameter across face.*—80 to 95 mm.

Corolla of ray florets:

*Color (abaxial).*—25-4.

*Color (adaxial).*—25-2.

Corolla of disc florets:

*Color.*—22-8 (immature) to 26-6 (mature).

Reproductive organs:

*Androecium.*—Present disc florets only.

*Gynoecium.*—Present both ray and disc florets.

PLANT

General appearance: semi-spreading branching pattern; medium height.

Foliage:

*Color (abaxial).*—Approximately 19-15.

*Color (adaxial).*—Approximately 19-13 to 19-14.

Frost and particularly characterized as to uniqueness by the combined characteristics of spoon daisy capitulum type; flat capitulum form; medium yellow ray floret color; yellow green (immature) to yellow (mature) disc floret color; diameter across face of capitulum from 80 to 95 mm. at maturity; uniform nine week flowering response to photoperiodic short-day control; medium plant height; semi-spreading branching pattern; and minimal pollen development.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7-10 f.c. | To Sept. 15 on - 5:30 PM Off - 7:30 AM | From Oct 15 300 ppm |
| WINTER | 58° F to 62° F | 65° F to 70° F | 60° F to 65° F | 2 to 5 weeks at 5 Hours Per Night of 7-10 f.c. | None | 300 ppm |
| SPRING | 58° F to 65° F | 65° F to 80° F | 60° F to 75° F | 2 to 4 weeks at 5 Hours Per Night of 7-10 f.c. | From Mar. 15 on - 5:30 PM Off - 7:30 AM | To Apr. 15 300 ppm |
| SUMMER | 62° F to 68° F | 70° F to 90° F | 65° F to 75°.F | 1 to 2 weeks at 3 Hours Per Night of 7-10 f.c. | On - 6:00 PM Off - 8:00 AM | NONE |

CHART B

COMPARISON OF YELLOW FROST AND FROST

| CULTIVAR | RAY FLORET COLOR | DIAMETER ACROSS FACE OF CAPITULUM | PLANT HEIGHT | BRANCHING PATTERN | FLOWERING RRSPONSE PERIOD | CAPITULUM FORM AND TYPE |
|---|---|---|---|---|---|---|
| Yellow Frost | Medium Yellow | 80 to 95 mm. | Medium | Semi-spreading | 9 week | Flat Spoon Daisy |
| Frost | White | 80 to 95 mm. | Medium | Semi-spreading | 9 week | Flat Spoon Daisy |

COMPARISONS MADE OF PLANTS GROWN IN A GREENHOUSE IN BARBERTON, OHIO UNDER ENVIRONMENTAL CONDITIONS AS DESCRIBED IN CHART A.

We claim:

1. A new and distinct cultivar of *Chrysanthemum morifolium* Ramat., known by the cultivar name Yellow

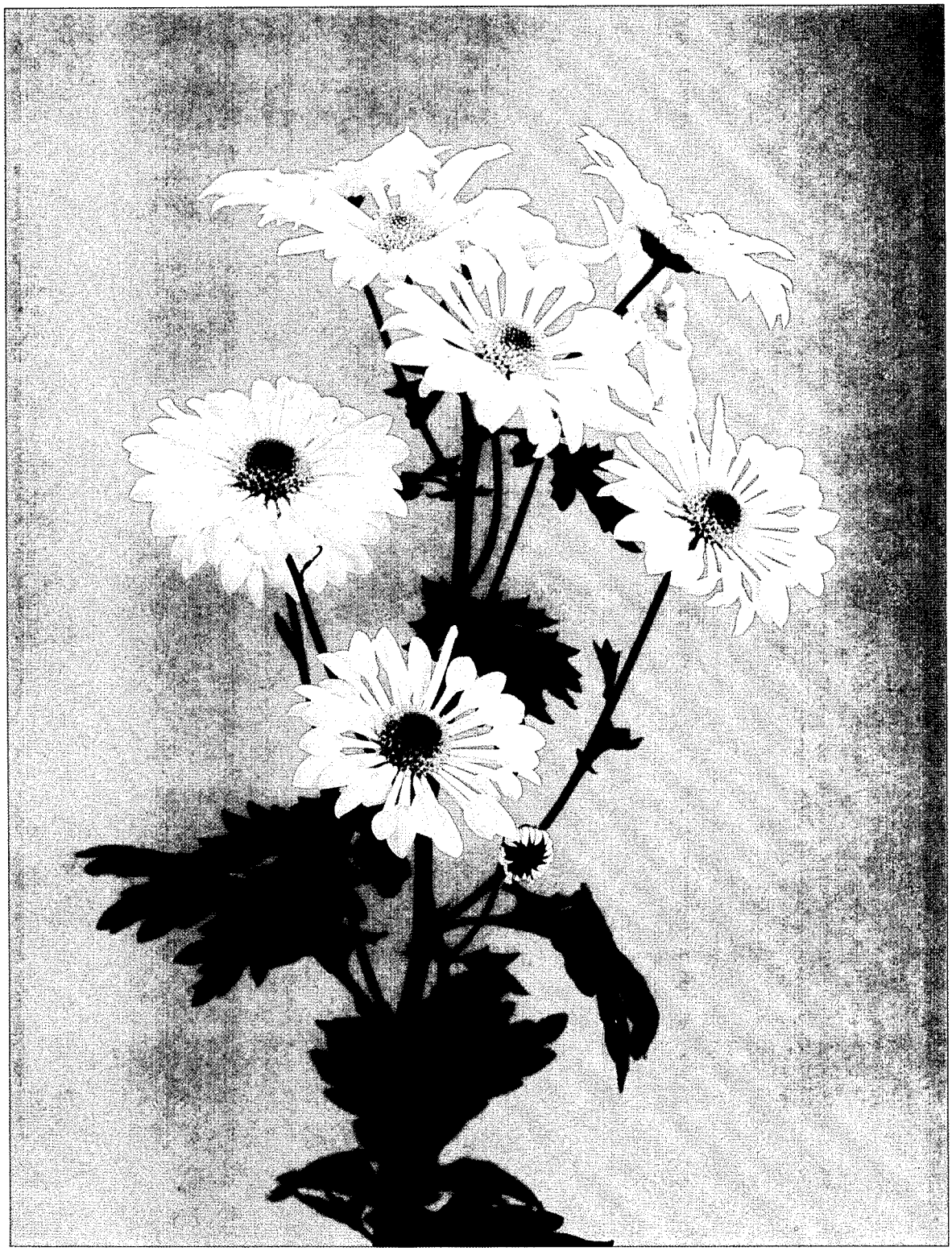

* * * * *